United States Patent

Karami et al.

[11] Patent Number: 5,308,313
[45] Date of Patent: May 3, 1994

[54] VENTED WOUND DRESSING

[75] Inventors: Hamzeh Karami; Thomas H. Gilman, both of Mansfield, Mass.

[73] Assignee: The Kendall Company, Mansfield, Mass.

[21] Appl. No.: 945,052

[22] Filed: Sep. 15, 1992

Related U.S. Application Data

[63] Continuation of Ser. No. 738,983, Jul. 29, 1991, abandoned.

[51] Int. Cl.⁵ .............. A61F 13/00; A61F 15/00; A61F 13/02; A61L 15/00
[52] U.S. Cl. ........................ 602/55; 602/54; 602/58; 602/59; 604/304; 604/307
[58] Field of Search .......... 128/888; 602/41–43, 602/47, 52, 54–56, 58–59; 604/304, 307

[56] References Cited

U.S. PATENT DOCUMENTS

| | | | |
|---|---|---|---|
| 797,094 | 8/1905 | Benario | 604/307 |
| 974,295 | 11/1910 | Pond | 604/304 |
| 2,399,545 | 4/1946 | Davis | 602/59 |
| 2,817,335 | 12/1957 | Thompson | 604/304 |
| 2,940,868 | 6/1960 | Patchell | 602/55 |
| 4,541,426 | 9/1985 | Webster | |
| 5,010,883 | 4/1991 | Rawlings et al. | |
| 5,018,515 | 5/1991 | Gilman | 602/55 |
| 5,056,510 | 10/1991 | Gilman | 604/307 |

FOREIGN PATENT DOCUMENTS 0020808 of 1897 United Kingdom ............... 604/307

*Primary Examiner*—David Isabella
*Assistant Examiner*—P. Zuttarelli
*Attorney, Agent, or Firm*—Alvin Isaacs

[57] ABSTRACT

A vented wound dressing is disclosed comprising a thin conformable sheet material at least a portion of the surface area of which is intended for placement as a dressing over a wound, which portion carries a pressure-sensitive adhesive coating on one surface thereof for adhering the dressing to skin, the coating being applied to provide repeating areas of the sheet material containing no adhesive, at least a portion of the repeating areas of no adhesive having slits extending through the thickness thereof to permit transfer of wound fluids through the sheet material unimpeded by presence of adhesive material which can clog the slits and thereby inhibit fluid transfer therethrough.

12 Claims, 2 Drawing Sheets

VENTED WOUND DRESSING

This is a continuation of application Ser. No. 07/738,983, filed Jul. 29, 1991, now abandoned.

BACKGROUND OF THE INVENTION

It is most desirable in wound treatment to provide an adhesive dressing which will maintain the desired moist environment promoting healing while preventing scab formation; and also permitting removal of wound fluid which can build up to a pressure bubble beneath the dressing, thereby undermining the adhesive seal to the skin and thus increasing the possibility of the wound being contacted by ambient contaminants, including, of course, microorganisms which can cause infection.

Seemingly, these two objectives are often at cross-purposes so that one of the two desired objectives is accomplished to the detriment of the other.

Yet, dressings fulfilling both objectives are heretofore disclosed in the art.

By way of illustration, reference is made to U.S. Pat. No. 4,541,426 issued to Webster whose discussion of the prior art as background to the invention is additionally worth mentioning.

As stated in Col. 1 of the patent:

It has long been a recognized problem that dressings are inclined to suffer from either or both the disadvantages that they sometimes tend to float away from a wound or else they sometimes tend to adhere to the wound surface.

The first of these disadvantages generally occurs when the wound is one that produces large volumes of exudate. Generally the method of overcoming this problem is to provide the dressing with holes so that the exudate can escape and the dressing remain in contact with the wound. Certain attempts to achieve this end are disclosed in U.K. Pat. Nos. 778813, 1298011, 1408345 and Patent Application Nos. 2061732 and 2074029. One successful dressing is Melolin (Trade mark available from T. J. Smith & Nephew Ltd., Hull, U.K.) which comprises a perforated synthetic polymer film and an absorbent cellulosic pad. The perforated film is placed next to the exuding wound, the exudate passes through the perforations and is absorbed by the pad. A more recent suggestion has been to use a perforated polytetrafluoroethylene film in an effort to minimise the risk of any adherency of the dressing to the wound.

Alternatively dressings have been suggested which comprise a thin hydrophobic film laminated to a fibrous absorbent layer. The film contains a number of apertures in the form of slits. Such dressings are described in, for example, British Pat. Nos. 815,121 and 1,163,452 and U.S. Pat. No. 3,602,220. However dressings of that type have not been found to be satisfactory because either the slits don not open or do not open wide enough to allow passage of exudate through the film to the absorbent.

The second of the aforementioned disadvantages generally occurs when the wound has dried out due to lack of production of exudate. Generally the method of overcoming this problem is to provide the dressing with a continuous layer which retards the rate of loss of water. One effective method of achieving this end is described in British Pat. No. 1280631.

However none of the known methods are free of disadvantages since what may be an excellent dressing for one kind of wound will be unsuitable for many other wounds since wounds differ greatly in their output of exudate. It has now been realised that, not only is there a need for a dressing which is suitable for use on a number of different wound types, there is also a need for a dressing which can better cope with the variation in rate of exudate production from a given wound. A dressing has now been discovered which allows passage of a greater amount of exudate from a wound which produces greater amounts of exudate and which aids in allowing the wound to remain a moist wound when it produces only smaller amounts of exudate so that it does not float away from the moist surface and has a reduced tendency to adhere to the wound. The new dressing has been found to aid in the re-epithelialisation of the wound.

Accordingly, the patented invention is said to provide a dressing comprising a conformable film with aperatures therethrough characterized in that the film comprises a first layer laminated to a second layer, the first layer comprising a material which swells when in contact with water and the second layer comprising a material which when in contact with water does not swell or swells less than the first layer. According to the patentee the apertures are enlarged when in use on a wet surface and otherwise not enlarged, the enlarged openings permitting passage of water, e.g. wound exudate, the apertures when not enlarged preventing the wound from drying out; i.e. providing a moist environment.

A particularly efficacious wound dressing permitting removal of wound fluids while maintaining a moist environment is described and claimed in copending application, Ser. No. 337,591 filed Apr. 13, 1989 and now U.S. Pat. No. 5,106,362.

As discussed in the copending application, the dressing will comprise: a base sheet for contacting the skin, the base sheet having an opening for placement over a wound and adhesive means for securing the base sheet to the skin; and vent means for providing controlled leakage of fluid along a path from the wound through the opening of the base sheet, the vent means comprising cover means covering the opening, the cover means permitting passage of wound fluid therethrough while reducing evaporation through the opening and thereby helping to insure a moist environment when excess wound fluid is removed from the wound.

The task of the present invention is to provide a wound dressing of simplified design and construction which permits removal of of wound fluids while at the same time maintaining a moist environment promoting wound healing.

BRIEF DESCRIPTION OF THE INVENTION

In accordance with the present invention it has been found quite unexpectedly, contrary to the teachings of the aforementioned Webster patent (to be discussed in more detail hereinafter) that the task may be solved in an elegant manner by providing a wound dressing comprising a thin conformable sheet material for placement over a wound, the sheet material carrying a pressure-sensitive adhesive layer on one surface thereof for adhering the dressing to the skin, the adhesive layer being applied so as to provide repeating areas of the sheet material containing no adhesive, at least a portion of the repeating areas free of adhesive having a slit extending through the thickness thereof to permit transfer of wound fluids through the sheet material unimpeded by the presence of adhesive.

DETAILED DESCRIPTION OF THE INVENTION

Figure 1:
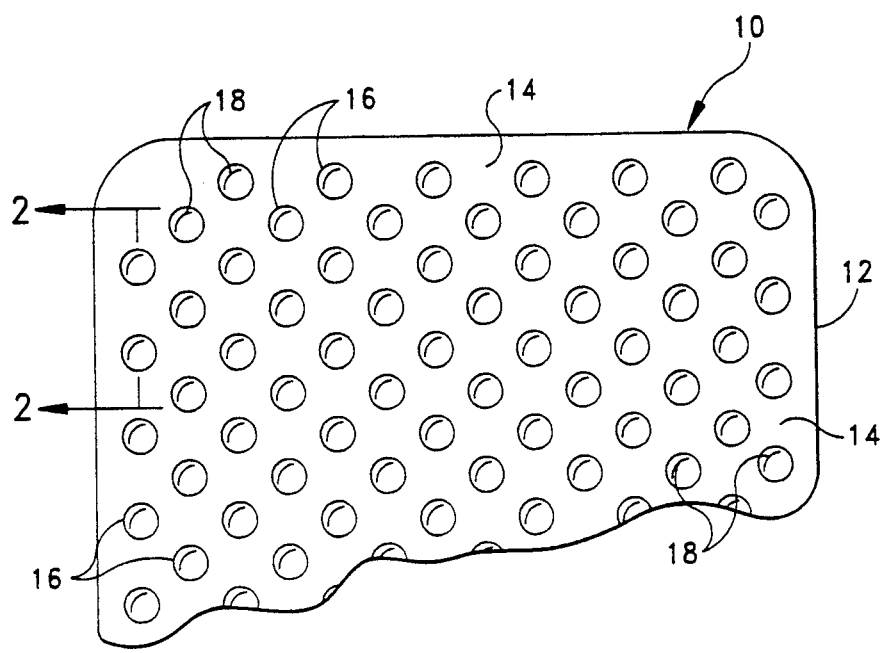
FIG. 1 is a plan view of the adhesive-bearing surface of a wound dressing of this invention.

As heretofore mentioned, it is most desirable to provide an adhesive dressing which will maintain a moist environment promoting healing while preventing scab formation; while at the same time permitting removal of excessive wound fluid which can cause a pressure build-up beneath the dressing to undermine the adhesive seal of the dressing to the skin and thereby increase the possibility of the wound being contacted with ambient contaminants.

Applicant's aforementioned U.S. Pat. No. 5,106,362 is directed to a particularly efficacious wound dressing satisfying these objectives. Yet, it is still desirable to provide a wound dressing meeting the above-noted criteria which is of simplified design and thus of lower cost to manufacture.

The aforementioned U.S. Pat. No. 4,541,426 of Webster is directed to what is described as a conformable apertured film which it is said (Col. 1) "allows passage of a greater amount of exudate . . . and which aids in allowing the wound to remain a moist wound when it produces only small amounts of exudate . . . ."

This is said to be accomplished by providing a dressing having two layers laminated together, the first layer 1 (to be placed on the wound) being water-swellable, the second layer 2 being non-swellable. As described and seen clearly in the patent drawings, the laminar structure is provided with slits 4 extending through the thickness of the two layers. An absorbent pad 6 may be positioned over the non-swellable second layer 2 and a layer of adhesive 5 may be provided along two opposed edges to adhere the dressing to the skin.

The slitted dressing of Webster is said to be an improvement over prior art slitted dressings such as the dressings described and claimed in U.S. Pat. No. 3,602,220 which are stated in Webster to be unsatisfactory because either the slits do no open or do not open wide enough to allow passage of exudate through the film to the absorbent.

Applicant concurs with this assessment by Webster of the prior art slitted dressing.

Such dressings do not of necessity contain an adhesive layer under the slits because such a layer would be a barrier to diffusion of exudate from the wound to the slitted sheet material and, moreover, would clog up the slits, thus acting in the nature of a dam precluding diffusion of the exudate therethrough.

Yet, Applicant has discovered that for proper operation of the opening of the slits to permit passage of exudate, it is essential (absent some chemical or physical action as described in Webster) for there to be a build-up of fluid pressure beneath the slits to force them to open. Since there is no adhesive beneath the slits, the exudate will leak out laterally and, consequently, there can be little if any pressure build-up for efficient opening of the slits.

Webster proposes in his patent that a dressing may be made having an adhesive coating on layer 1, the swellable layer. He states that "the adhesive may be applied over the entire surface of the first layer . . . " (Col. 5, line 62). He then goes on to state that "Alternatively the adhesive layer may be confined to a strip around the periphery of the dressing or to strips on two opposite edges of the dressing. This limited area of adhesive is not preferred."

A dressing embodying the invention of the Webster patent has been marketed by the assignee, Smith & Nephew under the trademark "TransSite", which dressing is the one stated to be least preferred, i.e., the one having two adhesive strips on opposite edges of the dressing. It is believed that there are two factors precluding commercialization of the design stated to be preferred: (1) it is not possible to laminate an adhesive to the swellable film without delamination occurring when the film swells; and (2) the adhesive coating will tend to keep the slits from opening, since the adhesive will flow and "mend the slit after it is made.

From what has been stated, it will be seen that while an adhesive coating beneath the openings of a slitted or perforated dressing is inoperable and thus contraindicated by the state of the art, Applicant has discovered that such an adhesive coating is nevertheless necessary (absent some other mechanism) to provide optimum transfer of the exudate through the openings of the dressing.

Having determined the necessity of a pressure build-up induced by the presence of an adhesive layer retaining the dressing securely against the skin so as to preclude lateral leaking or diffusion of exudate, the essence of the present invention is the discovery that the paradox or seeming impossibility of having the adhesive to provide the requisite pressure build-up to optimize fluid transfer through the slits without inhibiting the transfer therethrough by the very presence of the adhesive can be obviated by providing the adhesive coating in such a way that there are repeated voids in the coating providing areas free of adhesive and then slitting the thin sheet material in these non-adhesive areas. Preferably the non-adhesive areas are arranged in a uniform geometric pattern, e.g. in a series of rows covering the entire surface area of at least that portion of the sheet material intended to cover the wound.

The invention may best be understood by reference to the illustrative drawings taken in conjunction with the following detailed description.

Figure 2:
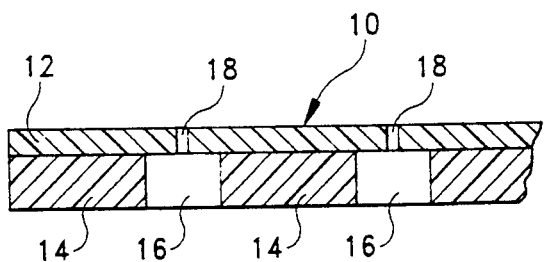
FIG. 2 is a sectional view taken along lines 2—2 of FIG. 1.

With reference to FIGS. 1 and 2, the novel vented wound dressing 10 of this invention will comprise a thin conformable sheet material 12, at least a portion of which is adapted for placement over a wound. At least the portion adapted for placement over a wound has a pressure-sensitive adhesive layer 14 on one surface thereof, the adhesive layer being applied to provide repeating spaced areas 16 free of adhesive. Preferably the non-adhesive areas 16 are arranged in a geometric pattern, e.g. in staggered rows as shown in the drawing. In any case, while the non-adhesive areas 16 are shown for purposes of illustration as being generally circular, the configuration is not critical and they may any desired shape, e.g. oval, rectangular, arcuate, etc.

Slits 18 are shown to be provided within each of the spaces defined by the non-adhesive areas. However, as heretofore stated, it is within the scope of this invention to provide slitsin only a portion of the non-adhesive areas. While shown in FIG. 1 to be somewhat arcuate in shape, slits 18 may have other forms and, as shown for example in the aforementioned U.S. Pat. No. 4,541,426 of Webster, they may be linear or in the form of triangular flaps provided by slitting two sides of the triangle, so that the flaps remain attached by the third side.

As heretofore mentioned, the novel dressings of this invention contemplate a sheet material at least a portion of which is adapted for placement on a wound, that portion having the described adhesive layer and slits. For purposes of illustration, in the embodiment illustrated in FIG. 1 the entire surface area of the dressing is adapted to cover a wound and the adhesive and the non-adhesive areas with the slits accordingly extend to the edges of sheet material 12 defining the periphery of the dressing.

Figure 3:
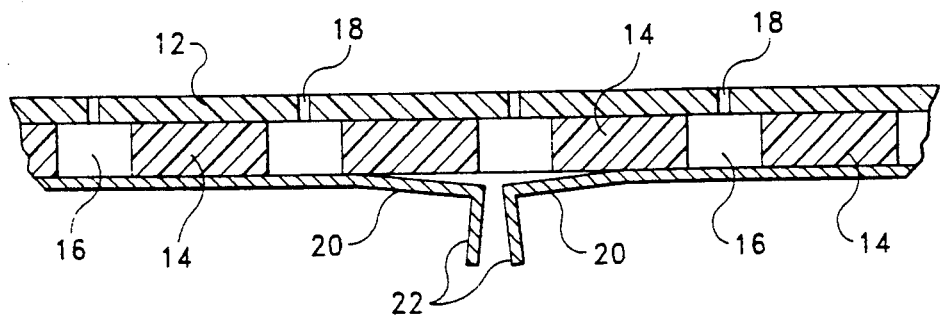
FIG. 3 is a sectional view of a preferred dressing of this invention having a release sheet covering the adhesive-bearing surface of the dressing.

FIG. 3 illustrates a preferred embodiment wherein a per se known release sheet covers the adhesive layer prior to use in order to prevent premature unwanted contact of the adhesive-bearing surface. In the form illustrated in the drawing the release sheet consists of a pair of contiguous sheets 20 which together cover the entire adhesive-bearing surface of sheet material 12. As seen, release sheets 12 may have free folded ends 22 for ease of gripping with the fingers to separate sheets 20 from the dressing.

While FIGS. 1 and 2 illustrate the essential novel features of the present invention, i.e. the features upon which patentable novelty is herein predicated, the wound dressings will preferably also include an absorbent pad or other per se known equivalent fabric positioned on the non-adhesive bearing surface, i.e. above the dressing, to provide a reservoir for receiving and retaining wound fluids diffusing through the slits 18. Preferably, a cover sheet providing a bacterial barrier is situated over the fabric reservoir. Various materials and arrangements of elements providing this function are of course well known in the wound dressing art and consequently per se comprise no part of this invention.

However, a particularly efficacious arrangement of elements providing a reservoir for receiving and retaining wound exudate contemplated for use in combination with the novel vented dressing of this invention is that described and claimed in Applicant's copending application, Ser. No. 461,598 filed Jan. 5, 1990 and now U.S. Pat. No. 5,060,642. As disclosed therein, the wound dressing has a sealed absorbent fabric design and structure wherein an absorbent fabric providing a reservoir for retaining wound exudate is contained between a bottom liquid-permeable sheet material permitting the wicking or diffusion of wound exudate and an outer cover characterized as being a bacterial barrier, at least a portion of the outer cover also being air-permeable for permitting egress of air from the interstices or voids in the fabric reservoir to the ambient atmosphere. As stated therein, this removal or displacement of entrained air within the fabric reservoir is necessary to free these interstices to act as a sponge for retention of wound fluid diffusing thereto, thereby appreciably increasing the capacity of the reservoir for receiving wound fluids.

Figure 4:
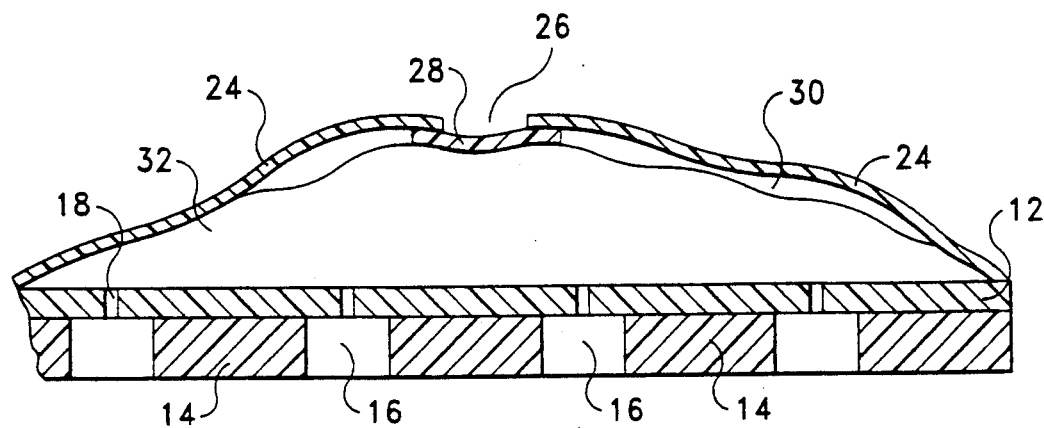
FIG. 4 is a fragmentary sectional view of another preferred embodiment of the invention.

FIG. 4 illustrates this preferred embodiment of the invention.

As shown, an absorbent pad or other absorbent fabric 32 is seated on the surface of sheet 12 opposed from the adhesive-bearing surface. The absorbent fabric 32 is covered with a liquid- and bacteria-impermeable cover sheet 24. Cover sheet 24 and sheet 12 are sealed in liquid- and bacteria-tight relationship around their common periphery so that exudate cannot escape through the edges of the dressing, nor can any external contaminants, including bacteria enter into the dressing and then pass through the slits 18 in sheet material 12 and then to the underlying wound.

The outer cover 24 is provided with one or more windows or openings 26 to permit egress of air from the interstices of the fabric reservoir 32 as well as the space 30 between the reservoir 32 and cover sheet 24. Each such window or opening is shown to be covered by an air-permeable bacterial barrier sheet 28 of slightly larger dimensions than the dimensions of opening 26. Each sheet 28 is sealed around its periphery to the edges of sheet 24 around opening 26 so as to prevent ingress of bacteria around the edges of the opening.

The particular materials employed for preparing sheets 24 28 and reservoir 32 may be selected from those heretofore known in the art for providing their respective functions. Since such materials are well known and their selection will be a matter of choice within the expected judgement of the skilled worker in the light of the foregoing description, their selection per se accordingly comprises no part of this invention.

Water-impermeable sheet 24 should as stated be impermeable to bacteria as well. It may, for example, be on the order of 0.5 to 1.0 mil thick and comprise a suitable polymeric material such as polyurethane, "Saran" (trademark of Dow Chemical), a polyolefin such as polyethlene or polyproplylene, a polyester such as polyethylene terephthalate, etc. In any event, sheet 24 should also be flexible and conformable.

Bacterial barrier 28 may comprise any of the per se known bacterial barrier air filters such as NUCLEOPORE, MILLIPORE, GELLMAN, etc.

Reservoir 32 may comprise any of the fabric materials heretofore employed for wound dressings to retain exudate, e.g. cotton, gauze sponges, absorbent pads such as those customarily used for abdominal surgery, and the like. If desired, they may additionally contain an antimicrobial agent such as chlorhexidine, although the use of such a reagent is not considered necessary.

In the embodiment illustrated in FIGS. 1 and 2, the entire surface area of the dressing is adapted for placement over the wound and the slits (and adhesive/non-adhesive areas extend to the edges of the dressing. However, as previously stated, the present invention contemplates wound dressings wherein only a portion of the sheet material constituting the dressing is intended to be placed on a wound.

Figure 5:
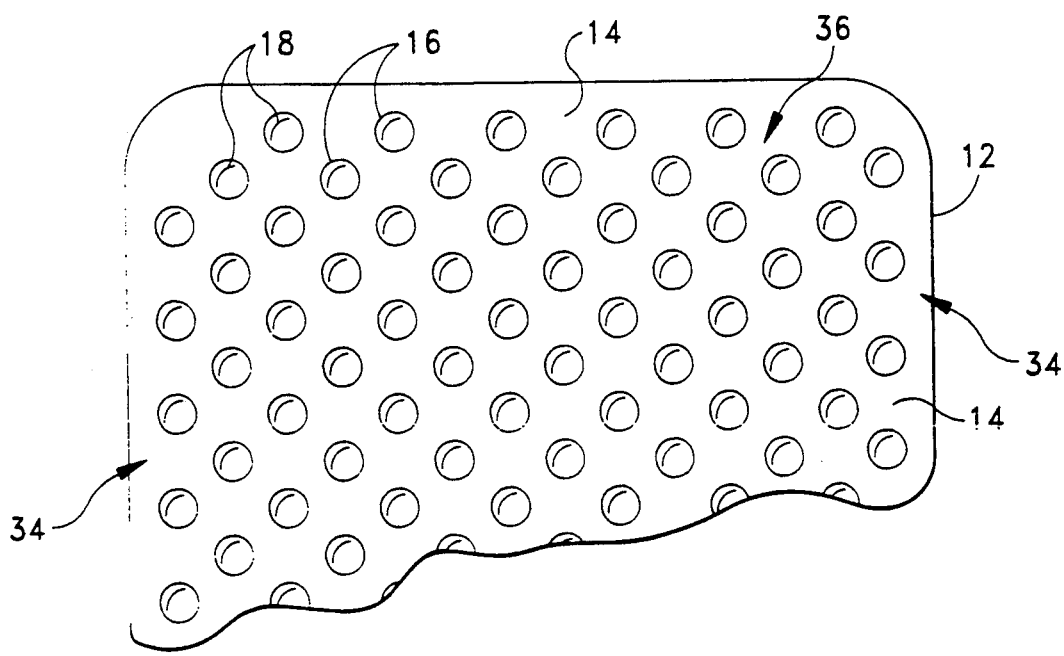
FIG. 5 is a fragmented plan view of a particularly preferred embodiment of the invention.

FIG. 5 is directed to a particularly preferred aspect of this invention embodying the latter concept.

As shown therein, a layer of pressure-sensitive adhesive 34 (which may be the same as or different from adhesive 14) is applied around the edges or periphery of sheet material 12, the adhesive 34 in turn defining the periphery of the portion of the dressing adapted for placement on the wound. Securing the dressing to the skin around its periphery in this manner serves to maintain the barrier function of the dressing against bacteria and other external contaminants as well as helping to insure that no wound exudate leaks out of the dressing laterally.

As heretofore mentioned, sheet 12 is flexible so as to be conformable to the contour of the body part to which it is to be applied. It may, for example, be as thin as 0.5 mil or as thick as 5.0 mil, but is preferably on the order of 1.0 mil thick. Preferably it is an elastomer which is characterized as being non-swellable or only slightly swellable. Materials useful for preparing slitted sheet 12 are well known in the art and will be readily suggested to those skilled in the art in the light of the foregoing description. By way of example, useful materials will include polyurethane, copolyesters such as "HYTREL", polyvinyl chlorides, polyolefins, etc.

The adhesive materials employed for preparing layer 14 and the peripheral coating 34 (FIG. 5) may likewise be any of the known so-called medical grade or hypoallergenic adhesives heretofore employed in securing dressings to the skin. Such known adhesives include the rubber-based, acrylic, vinyl ether and hydrocolloid pressure-sensitive adhesives. The adhesive may be applied to provide a layer of at least 1 mil thick, but preferably layers of adhesive at least 5 mils thick, e.g. on the order of 5-10 mils, are contemplated.

As was heretofore alluded to, the present invention is predicated upon the initial discovery that an adhesive layer is essential to provide to requisite pressure build-up to open the slits in a slitted dressing. In accordance with this invention, the adhesive-free areas containing the slits for transfer of wound exudate are isolated by adhesive coating forming a dam or barrier inhibiting lateral diffusion of the exudate so that it is instead directed upwardly through the slits provided in the dressing sheet. For optimum effectiveness, the ratio of surface area of the portion of sheet 12 adapted for placement on the wound which contains adhesive to the surface area which does not should be at least 1:1, i.e. at least 50% of the surface area of that portion should contain adhesive.

The non-adhesive areas in theory need not be any larger than the slits to be provided therein. However, to provide optimum manufacturing tolerance for the slitting operation to be sure the slits do not at least in part inadvertently overlap into the adhesive area, it has been found that the non-adhesive areas should be at least on the order of about ⅛ inch wide in the directions of the slit. For example, if the non-adhesive areas are circular, they should have a ⅛ inch diameter; and if they are square the length and width should be on the order of ⅛ inch. In any case, one skilled in the art will understand that the minimal dimensions will depend primarily upon the preciseness of the manufacturing equipment to provide the slits accurately in the prescribed non-adhesive areas.

In addition to permitting diffusion of wound exudate away from the wound and through the slits, it is essential that the wound dressings of this invention provide a barrier to evaporation of water (as distinguished from a barrier to removal of exudate) so as to keep the wound surface moist as excess exudate is removed.

The benefits of maintaining a moist wound surface are of course well known and include faster reepithelialization, less pain and better cosmetic results.

In order to do so, in accordance with the present invention the size and number of slits in the dressing should be such as to provide a dressing of the type known in the art as a moist healing wound dressing. In order to do so in accordance with this invention the size and number of slits should be such as to maintain a moisture vapor permeability or transition rate for the dressing of no greater than 1500 grams/meter/24 hours at 37° C. and 50% relative humidity.

By way of illustration, successful results have been obtained by providing 5-8½″ diameter non-adhesive areas per square inch of surface area to obtain the preferred moist dressing.

The slits will optimally extend across the width or diameter of the non-adhesive areas. With ⅛″ diameter circular areas, excellent results have been obtained with cross slits across the diameter of the circle. Many other slit designs may also be employed. For example, equal success has been obtained with 3/64 inch radius half circle slits in ⅛ inch diameter circles as well as S-shaped slits in ⅛ inch diameter areas. As shown in the drawings, however, the slits will have dimensions smaller than the non-adhesive areas where they are positioned so that each slit can be said to occupy only a portion of each non-adhesive area containing a slit.

The vented dressing of this invention may be prepared in the following manner:

(1) apply an adhesive layer of the desired thickness by calendering, casting, etc. between two release sheets of differential affinity;

(2) punch holes of the desired configuration and spacing through the thickness of the resulting "sandwich";

(3) remove the release sheet of lesser affinity from the adhesive, leaving the other release sheet of greater affinity adhering to the opposed surface of the adhesive;

(4) apply the free adhesive surface to the surface of the desired elastomeric sheet;

(5) provide slits by cutting the sheet in areas where there is no adhesive, i.e. in those areas where holes had been punched through the adhesive "sandwich"; and (6) thereafter replace the release sheet having the holes punched through it with a new one free from holes, thereby providing a dressing as shown in FIG. 3.

The further steps required to provide dressings such as shown in FIGS. 4 and 5 will be readily apparent to those skilled in the art and need not be discussed in further detail.

From the foregoing description, it will thus be appreciated that the present invention provides a wound dressing of simplified design which permits removal of excess wound exudate while at the same time providing the desired moist environment promoting proper healing.

Since certain changes may be made without departing from the scope of the invention herein contemplated, it is intended that the foregoing description and accompanying drawings be taken as illustrative and not in a limiting sense.

What is claimed is:

1. A vented wound dressing comprising a thin conformable sheet material a portion of which is adopted for placement as a dressing covering a wound and skin surrounding the wound, the dressing having a periphery defined by opposed edges of the sheet material, the sheet material having opposed surfaces, one of the surfaces carrying a layer of a pressure-sensitive adhesive, the adhesive in that portion for placement on the wound being applied to provide repeating spaced areas containing no adhesive, at least a portion of only the repeating areas of the sheet material containing no adhesive having slits extending through the opposed surfaces of the sheet material to permit transfer of wound fluids through the sheet material unimpeded by a presence of adhesive material which can clog the slits and thereby inhibit fluid transfer therethrough, each of the slits having smaller dimensions than the repeating areas of the sheet material containing no adhesive whereby each slit occupies only a portion of the area containing no adhesive having a slit, the dimensions and number of the slits being such as to retain sufficient moisture to provide a moist healing wound dressing, the adhesive around the periphery of the sheet material being present as a continuous layer uninterrupted by repeating areas containing no adhesive for securing the dressing to skin, the continuous peripheral layer of adhesive defining the portion of the sheet material adapted for placement on a wound, the continuous peripheral layer of adhesive further maintaining a barrier function against bacteria and other external contaminants as well as helping to insure that no wound fluids escape laterally.

2. A vented dressing as defined in claim 1 wherein the slits are provided in substantially all of the areas containing no adhesive.

3. A vented dressing as defined in claim 1 including an absorbent fabric providing a reservoir having a capacity for receiving and retaining wound fluids disposed over the surface of the sheet material opposed from the surface of the sheet material containing the adhesive layer.

4. A vented dressing as defined in claim 3 wherein the absorbent fabric is contained between the slitted sheet material and an outer cover comprising a cover sheet characterized as being a bacterial barrier, at least a portion of the outer cover also being air-permeable for permitting egress of air contained in the reservoir, the egress of air therefrom appreciably increasing the capacity of the reservoir to receive wound fluids diffusing to the reservoir through the slits in the sheet material covering the wound.

5. A vented dressing as defined in claim 4 wherein the sheet material and the outer cover sheet positioned thereover have a common periphery and are sealed in liquid and bacteria-tight relationship around their common periphery so that wound fluids cannot escape laterally from the dressing, nor can any external contaminants, including bacteria, enter into the dressing and then pass through the slits in the sheet material to an underlying wound.

6. A vented dressing as defined in claim 5 wherein the cover sheet contains at least one opening to permit the egress of air from the reservoir, each opening in the cover sheet being covered by an air-permeable bacterial barrier sheet, each bacterial barrier sheet being sealed to the cover sheet surrounding the opening so as to prevent ingress of bacteria around edges of the opening.

7. A vented dressing as defined in claim 1 characterized in that the adhesive-free areas containing the slits are isolated by the adhesive layer and the adhesive layer forms a dam or barrier inhibiting lateral diffusion of wound fluid, whereby to cause the wound fluid instead to be directed upwardly through the slits in the sheet material.

8. A vented dressing as defined in claim 7 wherein the sheet material has a ratio of surface area of the portion of the sheet material adapted for placement on the wound which contains adhesive to surface area of that portion which does not contain adhesive is at least 1:1.

9. A vented dressing as defined in claim 7 wherein the slits extend in a direction within the non-adhesive areas and the non-adhesive areas containing the slits are at least on an order of $\frac{1}{8}$ inch wide in the direction of the slit.

10. A vented dressing as defined in claim 7 wherein the non-adhesive areas are substantially circular in configuration.

11. A vented dressing as defined in claim 10 wherein the non-adhesive areas have a diameter of at least on an order of $\frac{1}{8}$ inch.

12. A vented dressing as defined in claim 7 wherein the size and number of slits in the dressing maintain a moisture vapor permeability for the dressing of no greater than about 1500 grams/meter/24 hours at 37° C. and 50% relative humidity, whereby to provide what is characterized as being a moist healing wound dressing.

* * * * *